Dec. 29, 1953 R. S. MOORE Plant Pat. 1,235
ROSE PLANT
Filed Dec. 8, 1952
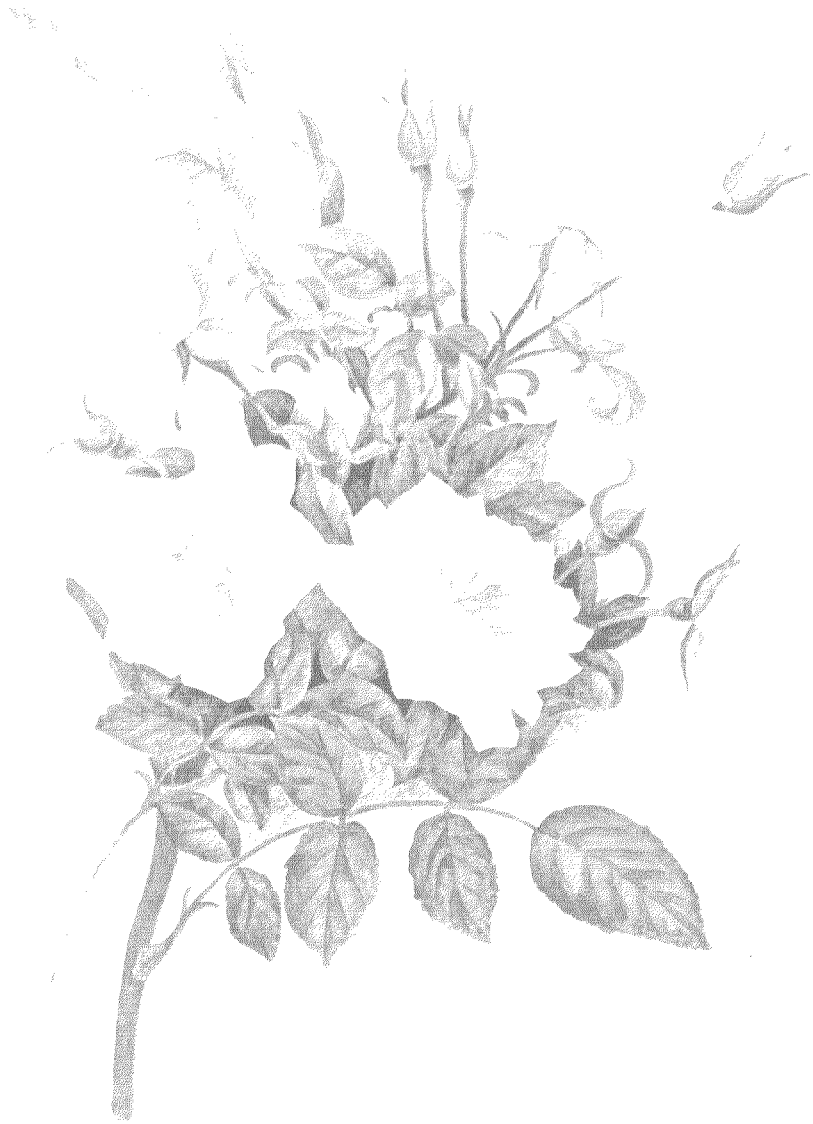
WITNESS
Gadison E. Avery
INVENTOR
RALPH S. MOORE
Webster & Webster
ATTYS.

Patented Dec. 29, 1953

Plant Pat. 1,235

UNITED STATES PATENT OFFICE 1,235

ROSE PLANT

Ralph S. Moore, Visalia, Calif.

Application December 8, 1952, Serial No. 324,863

1 Claim. (Cl. 47—61)

The present invention is directed to a new and distinct variety of ever-blooming climbing rose; the variety—as compared to the yellow climbing Cécile Brunner rose variety—blooming much more continuously; being substantially thornless, and having more lasting color in the flowers.

As distinguished from the pollen parent, Goldilocks Hybrid Polyantha (United States Plant Patent No. 672), the present variety bears flowers of a different shade of yellow (apricot yellow), and has practically no thorns.

In habit of growth, bloom, and thornlessness the present variety is generally similar to the Renae rose variety (United States Plant Patent No. 893).

The present variety is additionally characterized by being readily propagated; easy to grow when transplanted; and blooming in the first season in the garden.

An additional distinguishing characteristic of the present variety is that the flower buds are small, well shaped, and of an attractive apricot yellow color; being excellent in garden display, in small flower arrangements indoors, and in corsages.

In full bloom the flower of the present variety more closely approaches the size of the Cécile Brunner than that of the Goldilocks variety, the pollen parent.

A separate distinctive feature of the present variety of rose is that although a climber, it is more readily contained within a small space—such as on a trellis—than others of its type.

The present variety had the following breeding:

Pollen from flowers of the Goldilocks variety was used to pollinate an unnamed seedling, but which was a single flowered, climbing polyantha. Approximately one thousand seeds from this cross were planted, and of the resulting seedlings about one-quarter were climbing roses. These climbing roses were carefully observed, and one of these—the present variety—was noted to have the especially desirable characteristics described hereinbefore, and was thus selected for propagation.

Subsequent to its discovery and selection, the present variety has been successfully asexually reproduced by cuttings, and by budding; the reproductions having been found to carry forward each and every one of the desirable characteristics of the initial plant.

The breeding of the present variety, and its subsequent initial asexual reproduction thereof were accomplished by me in my nursery at Visalia, California.

In the drawings, the figure is a perspective view of flowers and buds of the variety, together with leaves and stem.

Referring now specifically to the new and distinct variety of rose plant, the following is a detailed description thereof in outline; all major color plate identifications being by Maerz and Paul Dictionary of Color.

Type: Seedling; climbing; outdoor for cut flowers or garden decoration.

Class: Hybrid, polyantha.

Flowers:

*Continuity.*—Continuous.

*Fragrance.*—Moderately sweet.

Flowers borne: Several to stem; in irregular cluster; on strong medium length stems.

Quantity of bloom: Abundant outdoors.

Bud:

*Peduncle.*—Short; slender; medium erect; medium green, reddish tinge.

*Before calyx breaks.*—Size—small. Form—pointed.

*As calyx breaks.*—Color—greenish yellow, overlaid with red.

*After first petal opens.*—Size—small. Form—long, pointed. Color—outside: apricot yellow (9–L–6) lightly overlaid with red tints (2–H–3); inside: apricot yellow (9–L–6).

Bloom: Size when fully opened, 2" to 2¼" average in diameter (occasionally 2½").

*Petalage.*—Double, with from 25 to 35 petals arranged irregularly.

*Form.*—Full, with petals loosely rolled outwardly.

Petals: Satiny.

*Shape.*—Outside oval, nearly egg shaped; intermediate, spatulate; inside, oblanceolate.

*Color.*—Apricot yellow (9–L–6), shading into a creamy yellow (9–D–1) when several days open.

*Flower longevity.*—Three to four days outdoors; two to three days indoors.

*Reproductive organs*

Stamens: Medium number; regularly arranged about pistils.

Filaments: Short; yellow.

Anthers: Small size; yellow.

Pollen: Moderate; yellow.

Pistils: Few.

Styles: Uneven; medium length; bunched.

Stigma: Greenish yellow.

Ovaries: Enclosed.

Hips: Usually none (few occasionally).
Sepals: Moderate length; spear shaped; green.

*Plant*

Foliage:
- *Leaves.*—Abundant; medium large; heavy; glossy.
- *Leaflets.*—Oval, with apex mucronate.
- *Base.*—Rounded.
- *Margin.*—Serrate.
- *Color.*—Mature leaves—upper surface: medium green (22–L–8); under surface: lighter green.
- *Rachis.*—Medium. Upper side smooth, grooved. Under side almost completely thornless.

Growth: Climbing; moderately vigorous.
- *Canes.*—Medium.
- *Main stems.*—Green (sometimes greenish-brown).
- *Thorns.*—Extremely few to none.
- *Prickles.*—None.
- *Branches.*—Green.
- *Thorns.*—Extremely few to none.
- *Prickles.*—None.
- *New shoots.*—Green (sometimes greenish-brown).
- *Thorns.*—Extremely few to none.
- *Prickles.*—None.

The climbing rose plant and its flowers as herein described may vary in slight detail due to climatic and soil conditions under which the variety may be grown.

Having thus described the invention, I claim:

A new and distinct variety of climbing hybrid polyantha rose plant, substantially as described and illustrated, characterized—in comparison to the climbing yellow Cécile Brunner rose variety, by blooming more continuously, being substantially thornless, and having more lasting color in the flowers; the buds and flowers being apricot-yellow in primary color, the buds being small and well shaped, and the flowers shading to a creamy yellow after several days open and being substantially the size of the flowers of said Cécile Brunner variety; being further characterized—in comparison to the pollen parent Goldilocks rose variety—by the apricot yellow primary color of the buds and flowers, and the substantial absence of thorns; and additionally characterized by being readily propagated, easy to grow when planted, blooming in the first season in the garden, and, although a climber, being readily contained within a small space, as on a trellis.

RALPH S. MOORE.

No references cited.